United States Patent [19]

Messersmith et al.

[11] Patent Number: 5,319,143
[45] Date of Patent: Jun. 7, 1994

[54] BIS(AMINOETHANETHIOLS)

[75] Inventors: David Messersmith, Cambridge; David P. Waller, Lexington, both of Mass.

[73] Assignee: Polaroid Corporation, Cambridge, Mass.

[21] Appl. No.: 923,859

[22] Filed: Jul. 31, 1992

[51] Int. Cl.$^5$ .......................................... C07C 323/24
[52] U.S. Cl. ..................... 564/500; 548/146; 564/430; 564/431; 564/434; 564/440; 564/461
[58] Field of Search ............... 514/665; 564/500, 501, 564/430, 431, 434, 440, 461, 504, 505, 506

[56] References Cited

U.S. PATENT DOCUMENTS

| | | | |
|---|---|---|---|
| 3,719,489 | 6/1971 | Cieciuch et al. | 96/29 D |
| 4,098,783 | 7/1978 | Cieciuch et al. | 260/147 |
| 5,248,826 | 9/1993 | Sasaki et al. | 564/434 |

FOREIGN PATENT DOCUMENTS

| | | | |
|---|---|---|---|
| 59-180548 | 10/1984 | Japan . | |
| 538195 | 4/1993 | Japan | 564/434 |

OTHER PUBLICATIONS

Felder et al., *Chem. Abs.*, vol. 55, No. 4, 3423 c-h (1961).

*Primary Examiner*—Richard L. Raymond
*Assistant Examiner*—Scott C. Rand
*Attorney, Agent, or Firm*—Carol A. Loeschorn

[57] ABSTRACT

There are disclosed certain bis(aminoethanethiols) and the salts thereof which find utility as intermediates in the preparation of certain dye-providing compounds useful in photographic imaging systems.

3 Claims, No Drawings

BIS(AMINOETHANETHIOLS)

BACKGROUND OF THE INVENTION (1) Field of the Invention

This application relates to bis(aminoethanethiol) compounds and salts thereof useful as intermediates in the preparation of image dye-providing materials for use in photographic applications.

(2) Description of the Related Art

U.S. Pat. No. 3,719,489 describes and claims photographic processes employing initially photographically inert compounds which are capable of undergoing cleavage in the presence of silver ions made available imagewise during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, dyes which are substantially nondiffusible in the photographic processing composition but capable of undergoing cleavage in the presence of the imagewise distribution of silver ions and/or soluble silver complex made available in the undeveloped and partially developed areas of a silver halide emulsion as a function of development to liberate a more diffusible dye in an imagewise distribution corresponding to the imagewise distribution of said ions and/or said complex. The formation of a color image is the result of the differential in diffusibility between the parent compound and the liberated dye whereby the imagewise distribution of the more diffusible dye released in the undeveloped and partially developed areas is free to transfer. Color-providing compounds useful in the above processes form the subject matter of U.S. Pat. No. 4,098,783, a continuation in part of said U.S. Pat. No. 3,719,489.

Among the color-providing materials disclosed in the aforementioned U.S. Pat. No. 4,098,783 are the thiazolidine dyes comprising a substituted or unsubstituted thiazolidine group and a complete dye, e.g.,

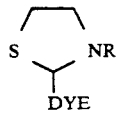

As described therein, these thiazolidine dyes can be prepared by condensing a dye-substituted aldehyde, i.e., DYE-CHO, with an aminoethanethiol, e.g.,

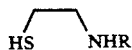

Copending application Ser. No. 923,843, filed Jul. 31, 1992 of M. Arnost, E. Chinoporos, D. McGowan and D. Waller, filed on even date herewith, discloses certain color-providing compounds, useful in the processes described in the aforementioned U.S. Pat. No. 3,719,489 and in thermally developed silver halide photographic processes such as disclosed in Japanese Kokai 59-180548, having a Laid-Open date of Oct. 13, 1984. A preferred embodiment of the color-providing compounds disclosed in the aforementioned copending application Ser. No. 923,843, filed Jul. 31, 1992 is represented by the formula

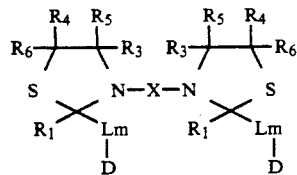

Formula I wherein D represents a complete dye, i.e., a dye radical of an organic dye; L represents a divalent organic linking group containing at least one carbon atom; m is 0 or 1; X represents a chemical linkage joining the two cyclic 1,3-sulfur-nitrogen groups; $R_1$ represents hydrogen, a monovalent organic radical or together with L represents the atoms necessary to complete a spiro union with one of the cyclic 1,3 sulfur-nitrogen groups when m is 1 or together with D represents the atoms necessary to complete a spiro union with one of the cyclic 1,3-sulfur-nitrogen groups when m is 0; and $R_3$, $R_4$, $R_5$ and $R_6$ are each independently hydrogen, a monovalent organic radical or taken together, $R_3$ and $R_4$ or $R_5$ and $R_6$ represent a substituted or unsubstituted carbocyclic or heterocyclic ring. Upon silver ion assisted cleavage, these color-providing compounds release a diffusible dye.

The present application is directed to bis(aminoethanethiol) compounds which are useful as intermediates in the preparation of the compounds of Formula I.

SUMMARY OF THE INVENTION

The present invention provides compounds which are useful as intermediates in the preparation of image dye-providing materials.

The present invention also provides novel bis(aminoethanethiol) compounds and the salts thereof. Because the compounds contain two aminoethanethiol moieties rather than one, they can be used for synthesizing image dye-providing materials possessing two color-providing moieties and two thiazolidine or benzothiazolidine moieties.

The invention accordingly comprises the products and compositions possessing the features, properties and relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

Specifically, the bis(aminoethanethiol) compounds of the present invention may be represented by the formula

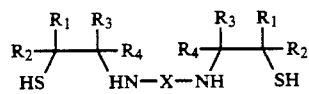

wherein $R_1$, $R_2$, $R_3$, and $R_4$ are each independently selected from hydrogen, alkyl, aryl, aralkyl and alkaryl or taken together $R_1$ and $R_3$ or $R_2$ and $R_4$ represent the atoms necessary to complete a substituted or unsubstituted saturated alicyclic ring system and X is a chemical linkage joining the two nitrogen atoms; and the salts thereof.

Typical aryl groups include phenyl and biphenyl and said alkyl groups comprising $R_1$, $R_2$, $R_3$, and $R_4$ usually contain 1 to 20 carbon atoms. Aralkyl may be, for example, phenyl-substituted alkyl wherein said alkyl usually contains 1 to 20 carbon atoms, and said alkaryl may be, for example, alkyl-substituted phenyl wherein said alkyl usually contains 1 to 20 carbon atoms.

The chemical linkage, X, may be a single covalent bond, as where the two nitrogen atoms are directly joined to each other by a shared pair of electrons, or it may be a bivalent organic group, i.e., an organic group having two free valences attached to different atoms and joined to each of the respective nitrogen atoms by single covalent bonds. Preferably, the chemical linkage, X, is a bivalent organic group.

As examples of suitable chemical linkages, X, within the scope of the present invention, mention may be made of the following:

(a shared pair of electrons);
—R—, wherein R is a bivalent hydrocarbon residue, e.g., alkylene or arylene usually containing 1 to 20 carbon atoms;
—R—O—R—;
—R—O—R', wherein R' is a bivalent hydrocarbon residue, e.g., alkylene or arylene usually containing 1 to 20 carbon atoms, different from R;
—R—O—R'—O—R—;
—R—O—R'—O—R"—, wherein R" is a bivalent hydrocarbon residue, e.g., alkylene or arylene usually containing 1 to 20 carbon atoms, different from R and R';
—Ar—CO—NH—R—O—R'—O—R—NH—CO—Ar—, wherein Ar represents aryl;
—R—CONH—R'—NH—CO—R—
—R—NH—SO$_2$—R—SO$_2$—NH—R—;
—R—NH—SO$_2$—R'—SO$_2$—NH—R—;
—R—NH—SO$_2$—R'—SO$_2$—NH—R"—;

The aryl, alkylene and arylene groups referred to above are intended to also include corresponding substituted groups.

The salts may be represented by the formula

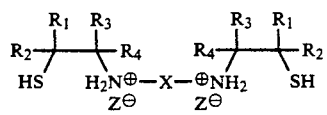

wherein $R_1$, $R_2$, $R_3$, and $R_4$ and X have the same meaning as above, and Z is an anion such as chloride, bromide, iodide, sulfonate, tetraphenylborate, etc.

The compounds of the invention can be prepared by reactions which are known in the art and these will be apparent particularly in view of the specific examples provided herein.

The following examples are given to further illustrate the present invention and are not intended to limit the scope thereof.

EXAMPLE 1

Preparation of the compound having the formula

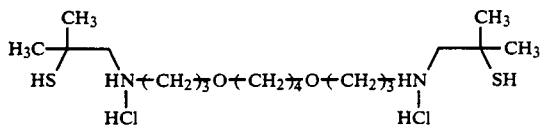

25 g of 1,4-bis(2-aminopropoxy)butane was stirred at room temperature in 250 mL of absolute ethanol while 25.2 g of the bis(isobutraldehyde) disulfide having the structure

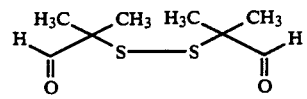

was added dropwise over 1.5 hours. The reaction was refluxed for 2 hours and then cooled. To the cooled solution was added 13.8 g of sodium borohydride. The resulting reaction mixture was stirred in a cold water bath overnight. 65 mL concentrated hydrochloric acid was added dropwise forming a white precipitate which was dissolved by the addition of 250 mL water. 12 g of zinc dust was introduced portionwise over several hours and the reaction was stirred overnight under nitrogen. The excess zinc was filtered and the ethanol was removed under reduced pressure. The resulting residue was diluted with water and extracted twice with n-butanol. The n-butanol was removed under reduced pressure and the product dissolved in a solution containing 250 mL of water and 30 mL of 10% hydrochloric acid. The aqueous solution was concentrated under reduced pressure to yield 24 g of the title compound. The structure was confirmed by NMR analysis.

The bis(isobutraldehyde) disulfide used above was prepared as follows:

To a solution of 57.8 g of isobutyraldehyde in 100 mL of chloroform at 25°C. was added dropwise 54 g of freshly distilled sulfur monochloride. The rate of addition was adjusted so as to maintain the temperature below 40° C. After the addition was complete, the chloroform was removed in vacuo and the residue was distilled to yield bis(isobutyraldehyde) disulfide, 81°-84° (0.4 mm). The structure was confirmed by spectral analysis.

The free base of the title compound was obtained by dissolving the title compound in water and neutralizing with an aqueous sodium bicarbonate solution. The free base was extracted into methylene chloride, dried, and concentrated. The structure was confirmed by spectral analysis.

The following compounds were prepared by the procedure of Example 1, substituting the appropriate bis-amino compound for 1,4-bis(2-aminopropoxy) butane. The structures were confirmed by NMR analysis:

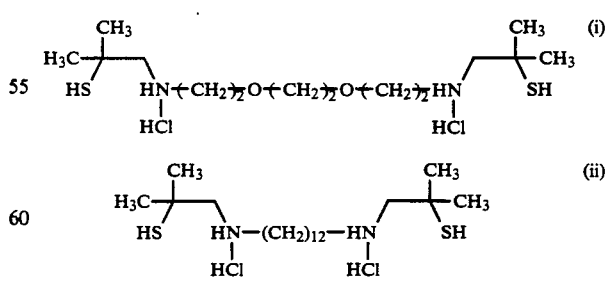

As noted above, the bis(aminoethanethiols) of the subject invention are useful as intermediates in the synthesis of photographic image dye-providing materials, such as, the compounds of Formula I, above, described in the aforementioned copending U.S. Pat. application Ser. No. 923,843, filed Jul. 31, 1992. For this purpose, the subject compounds or the salts thereof may be condensed with two equivalents of a dye-substituted aldehyde, i.e., DYE-CHO, or with two equivalents of an intermediate possessing an aldehyde group and the condensation product then reacted with the appropriate molecule or molecules to yield the final dye product. It will be appreciated that a dye-substituted ketone may be substituted for the dye-substituted aldehyde, particularly where it is desired to prepare spiro derivatives.

Since certain changes may be made in the herein described subject matter without departing from the scope of the invention herein involved, it is intended that all matter contained in the above description and examples be interpreted as illustrative and not in a limiting sense.

We claim:

1. A compound of the formula

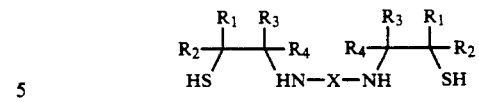

wherein $R_1$, $R_2$, and $R_4$ are each independently selected from hydrogen, alkyl having between 1 to 20 carbon atoms, phenyl, biphenyl, aralkyl wherein said alkyl portion has between 1 to 20 carbon atoms and said ara portion is a phenyl or bihenyl, alkaryl wherein said alkyl portion has between 1 to 20 carbon atoms and said aryl portion is a phenyl or biphenyl, or taken together $R_1$ and $R_3$ or $R_4$ represent the atoms necessary to complete a substituted or unsubstituted saturated alicyclic ring system and X is —R—O—R'—O—R— where R and R' are the same or different and represent bivalent hydrocarbon residues, and the salts thereof.

2. A compound according to claim 1, wherein R and R', the same or different, represent alkylene.

3. A compound having the formula

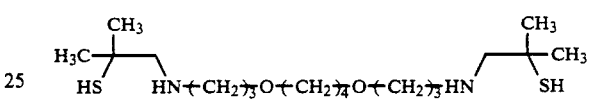

and the salts thereof.

* * * * *